US012593850B2

(12) United States Patent
Savion et al.

(10) Patent No.: US 12,593,850 B2
(45) Date of Patent: Apr. 7, 2026

(54) BACTERIOPHAGES FOR THE CONTROL OF BACTERIAL SPECK DISEASE

(71) Applicant: EcoPhage Ltd., Nes Ziona (IL)

(72) Inventors: Orly Savion, Ness Ziona (IL); Olga Nissan, Rehovot (IL); Sammy Frenk, Kfar Saba (IL); Rudy Maor, Hethersett (GB); Liat Avrahami-Moyal, Gan Yavne (IL)

(73) Assignee: EcoPhage Ltd., Nes Ziona (IL)

( * ) Notice: Subject to any disclaimer, the term of this patent is extended or adjusted under 35 U.S.C. 154(b) by 0 days.

(21) Appl. No.: 18/684,499

(22) PCT Filed: Aug. 17, 2022

(86) PCT No.: PCT/IL2022/050896
§ 371 (c)(1),
(2) Date: Feb. 16, 2024

(87) PCT Pub. No.: WO2023/021513
PCT Pub. Date: Feb. 23, 2023

(65) Prior Publication Data
US 2024/0324600 A1 Oct. 3, 2024

Related U.S. Application Data

(60) Provisional application No. 63/233,844, filed on Aug. 17, 2021.

(51) Int. Cl.
*A01N 63/40* (2020.01)
*A01P 1/00* (2006.01)
*C12N 7/00* (2006.01)

(52) U.S. Cl.
CPC ............... *A01N 63/40* (2020.01); *A01P 1/00* (2021.08); *C12N 7/00* (2013.01); *C12N 2795/00021* (2013.01); *C12N 2795/00031* (2013.01)

(58) Field of Classification Search
None
See application file for complete search history.

(56) References Cited

U.S. PATENT DOCUMENTS 10,499,651 B2 * 12/2019 Gonzalez ................. C12N 7/00
2008/0124305 A1 5/2008 Jackson et al.

FOREIGN PATENT DOCUMENTS

WO WO 2014/063070 A2 4/2014

OTHER PUBLICATIONS

Database NCBI [Online] Jan. 12, 2016 (Jan. 12, 2016). Pseudomonas phage CHF7, complete genome. GenBank accession No. MN729596. 1. (Year: 2016).*
Hernandez et al. Bacteriophage-Mediated Reduction of Bacterial Speck on Tomato Seedlings. Phage (New Rochelle). Dec. 1, 2020; 1(4):205-212. Epub Dec. 16, 2020. (Year: 2020).*
Whisstock J.C. et al. Prediction of protein function from protein sequence and structure. Q Rev Biophys. Aug. 2003;36(3):307-40. Review. (Year: 2003).*
Database NCBI [Online] Dec. 21, 2018 (Dec. 21, 2018). Pseudomonas phage vB_PaeS_SCUT-S4, complete genome. GeneBank accession No. LN913017.1. URL: https://www.ncbi.nlm.nih.gov/nucleotide/MK165658.1?report=genbank&log$=nuclalign&blast_rank=2&RID=J3KA58WX013. (Dec. 21, 2018).
Database NCBI [Online] Jan. 12, 2016 (Jan. 12, 2016). Pseudomonas phage CHF7, complete genome. GeneBank accession No. MN729596. 1. URL: https://www.ncbi.nlm.nih.gov/nucleotide/MN729596.1?report=genbank&log$=nuclalign&blast_rank=2&RID=J3JF9CUX016. (Jan. 12, 2016).
Flores, O. et al., (2020), "Characterization of Bacteriophages *Pseudomonas syringae* pv. Actinidiae with Potential Use as Natural Antimicrobials in Kiwifruit Plants," Microorganisms, 8(7), 974.# Jun. 29, 2020)).
Hernandez, C. A. et al., (2020), "Bacteriophage-Mediated Reduction of Bacterial Speck on Tomato Seedlings," PHAGE: Therapy, Applications and Research, 1(4), 205-212.Dec. 16, 2020 #).
PCT International Search Report and Written Opinion, PCT Application No. PCT/IL2022/050896, Sep. 29, 2022, 9 pages.

* cited by examiner

*Primary Examiner* — Cynthia E Collins
(74) *Attorney, Agent, or Firm* — Fenwick & West LLP

(57) ABSTRACT

Agricultural compositions are disclosed which comprise at least one isolated bacteriophage capable of infecting the plant pathogen *Pseudomonas syringae* pv. tomato, the at least one bacteriophage having a genomic nucleic acid sequence at least 85% identical to one of the nucleic acid sequence as set forth in SEQ ID NOs: 1-23. The composition comprises no more than 10 different strains of bacteriophage. Uses thereof for treating bacterial speck disease are also disclosed.

10 Claims, 4 Drawing Sheets

Specification includes a Sequence Listing.

BACTERIOPHAGES FOR THE CONTROL OF BACTERIAL SPECK DISEASE

RELATED APPLICATION

This application claims the benefit of priority of U.S. Provisional Patent Application No. 63/233,844 filed on 17 Aug. 2021, the contents of which are incorporated herein by reference in their entirety.

SEQUENCE LISTING STATEMENT

The ASCII file, entitled 93249 SequenceListing.txt, created on August 2022 15, comprising 1,160,062 bytes, submitted concurrently with the filing of this application is incorporated herein by reference.

FIELD AND BACKGROUND OF THE INVENTION

The present invention, in some embodiments thereof, relates to agricultural compositions comprising bacteriophages for the control of plant pathogens.

Bacteriophages are viruses that specifically infect bacteria. The emergence of antibiotic resistance and heavy metal tolerance in recent years resulted in a renewed interest in bacteriophage therapy in multiple fields, including human and livestock health and crop protection.

Within the crop protection disciplines, the prevention and treatment of bacterial diseases represent an increasing challenge. Damage caused by bacterial pathogens result in considerable loss yield which in turn cost farmers billions of dollars in annual revenues. Common agricultural practices include the application of chemical based compounds such as broad-spectrum antibiotics like streptomycin, or copper-based bactericides. However, in recent years the use of these compounds has been restricted in many regions due to their toxicity to plants and the environment along with insufficient efficacy acceptance and poor public opinion.

One major bacterial disease in tomato plants is bacterial speck disease caused by *Pseudomonas syringae* pv. tomato. Pathogen-related diseases can lead to yield losses of up to 60% and cause annual damages estimated in billions of dollars. Bacteria can spread from plant to plant by tools, workers' hands, or through splashing rain or irrigation water. Therefore, a preventative treatment, where the active ingredient (e.g., bacteriophage) is applied prophylactically can be especially useful in preventing and reducing the disease symptoms.

Background art includes U.S. Pat. No. 10,499,651; U.S. patent application Ser. No. 2008/0124305 and International Patent Application No. WO2014/063070. Agriphage™ is a product by Omnilytics which comprises bacteriophages for the control of bacterial spot (XCV) and bacterial speck (PST).

SUMMARY OF THE INVENTION

According to an aspect of the present invention there is provided an agricultural composition comprising:

(i) at least one isolated bacteriophage capable of infecting the plant pathogen *Pseudomonas syringae* pv. tomato, the at least one bacteriophage having a genomic nucleic acid sequence at least 85% identical to the nucleic acid sequence as set forth in SEQ ID NOs: 1, 2, 3, 4, 5, 6, 7 8, 9, 10, 11, 13, 14, 15, 18, 19, 20, 21 or 23; and (ii) an agriculturally acceptable carrier, wherein the composition comprises no more than 10 different strains of bacteriophage.

According to embodiments of the invention, the composition comprises no additional bacteriophage that infect plant pathogens other than *Pseudomonas syringae* pv. tomato.

According to embodiments of the invention, the agricultural further comprises an agent which promotes the growth of a plant or maintains the health of the plant.

According to embodiments of the invention, the agent is selected from the group consisting of a fertilizer, an acaricide, a herbicide, a fungicide, an insecticide, a nematicide, a pesticide, a plant growth regulator, a rodenticide and a nutrient.

According to embodiments of the invention, the agriculturally acceptable carrier comprises at least one agent selected from the group consisting of a stabilizer, a tackifier, a preservative, a carrier, a surfactant, an anticomplex agent and a combination thereof.

According to embodiments of the invention, the at least one bacteriophage capable of infecting *Pseudomonas syringae* pv. tomato comprises at least two non-identical bacteriophages capable of infecting *Pseudomonas syringae* pv. tomato.

According to embodiments of the invention, the agricultural composition comprises:

(i) a first bacteriophage having a genomic nucleic acid sequence at least 85% identical to the nucleic acid sequence as set forth in SEQ ID NO: 7; and (ii) a second bacteriophage having a genomic nucleic acid sequence at least 85% identical to the nucleic acid sequence as set forth in SEQ ID NO: 9.

According to embodiments of the invention, the agricultural composition further comprises a third bacteriophage having a genomic nucleic acid sequence at least 85% identical to the nucleic acid sequence as set forth in SEQ ID NO: 12.

According to an aspect of the present invention there is provided an article of manufacture comprising:

(i) a first bacteriophage capable of infecting the pathogen *Pseudomonas syringae* pv. Tomato, the bacteriophage having a genomic nucleic acid sequence at least 85% identical to the nucleic acid sequence as set forth in SEQ ID NOs: 1, 2, 3, 4, 5, 6, 78, 9, 10, 11, 12, 13, 14, 15, 16, 17, 18, 19, 20; 21, 22 or 23 and (ii) a second, non-identical bacteriophage capable of infecting the pathogen *Pseudomonas syringae* pv. tomato, the bacteriophage having a genomic nucleic acid sequence at least 85% identical to the nucleic acid sequence as set forth in SEQ ID NOs: 1, 2, 3, 4, 5, 6, 7, 8, 9, 10, 11, 12, 13, 14, 15, 16, 17, 18, 19, 20, 21, 22 or 23.

According to embodiments of the invention, the first bacteriophage has a genomic nucleic acid sequence at least 85% identical to the nucleic acid sequence as set forth in 1-11, 13-15, 18-20 and 22-23.

According to embodiments of the invention, the second bacteriophage has a genomic nucleic acid sequence at least 85% identical to the nucleic acid sequence as set forth in 1-11, 13-15, 18-20 and 22-23.

According to embodiments of the invention, the article of manufacture further comprises a third, non-identical bacteriophage capable of infecting the pathogen *Pseudomonas syringae* pv. tomato, the bacteriophage having a genomic nucleic acid sequence at least 85% identical to the nucleic acid sequence as set forth in SEQ ID NOs: 1, 2, 3, 4, 5, 6, 7 8, 9, 10, 11, 12, 13, 14, 15, 16, 17, 18, 19, 20, 21, 22 or 23.

According to embodiments of the invention, the first bacteriophage has a genomic nucleic acid sequence at least 85% identical to the nucleic acid sequence as set forth in SEQ ID NO: 7, the second bacteriophage has a genomic nucleic acid sequence at least 85% identical to the nucleic acid sequence as set forth in SEQ ID NO: 17 and the third bacteriophage has a genomic nucleic acid sequence at least 85% identical to the nucleic acid sequence as set forth in SEQ ID NO: 21.

According to embodiments of the invention, the first bacteriophage has a genomic nucleic acid sequence at least 85% identical to the nucleic acid sequence as set forth in SEQ ID NO: 17, the second bacteriophage has a genomic nucleic acid sequence at least 85% identical to the nucleic acid sequence as set forth in SEQ ID NO: 19 and the third bacteriophage has a genomic nucleic acid sequence at least 85% identical to the nucleic acid sequence as set forth in SEQ ID NO: 20.

According to embodiments of the invention, the first bacteriophage has a genomic nucleic acid sequence at least 85% identical to the nucleic acid sequence as set forth in SEQ ID NO: 7, the second bacteriophage has a genomic nucleic acid sequence at least 85% identical to the nucleic acid sequence as set forth in SEQ ID NO: 9 and the third bacteriophage has a genomic nucleic acid sequence at least 85% identical to the nucleic acid sequence as set forth in SEQ ID NO: 12.

According to an aspect of the present invention there is provided an method of controlling or preventing bacterial speck disease of a tomato plant comprising contacting the tomato plant with at least one bacteriophage in an amount which is effective at infecting the plant pathogen *Pseudomonas syringae* pv. Tomato, the at least one bacteriophage having a genomic nucleic acid sequence at least 85% identical to the nucleic acid sequence as set forth in SEQ ID NOs: 1, 2, 3, 4, 5, 6, 7 8, 9, 10, 11, 12, 13, 14, 15, 16, 17, 18, 19, 20, 21, 22 or 23, thereby controlling or preventing the bacterial speck disease of the tomato plant.

According to embodiments of the invention, the at least one first bacteriophage has a genomic nucleic acid sequence at least 85% identical to the nucleic acid sequence as set forth in 1-11, 13-15, 18-20 and 22-23.

According to embodiments of the invention, the contacting is affected at a seedling phase.

According to embodiments of the invention, the contacting is in the soil in the vicinity of or onto: a root, a stem, a seed, a fruit, a flower, a leaf, or any combination thereof.

According to embodiments of the invention, the contacting comprises dipping, spraying or fogging.

According to embodiments of the invention, the at least one bacteriophage comprises at least two bacteriophages, wherein a second of the at least two bacteriophages has a genomic nucleic acid sequence at least 85% identical to the nucleic acid sequence as set forth in SEQ ID NOs: 1, 2, 3, 4, 5, 6, 78, 9, 10, 11, 12, 13, 14, 15, 16, 17, 18, 19, 20, 21, 22 or 23.

According to embodiments of the invention, the at least one bacteriophage comprises at least three bacteriophages, wherein a third of the at least three bacteriophages has a genomic nucleic acid sequence at least 85% identical to the nucleic acid sequence as set forth in SEQ ID NOs: 1, 2, 3, 4, 5, 6, 78, 9, 10, 11, 12, 13, 14, 15, 16, 17, 18, 19, 20, 21, 22 or 23.

According to embodiments of the invention, the first bacteriophage has a genomic nucleic acid sequence at least 85% identical to the nucleic acid sequence as set forth in SEQ ID NO: 7, the second bacteriophage has a genomic nucleic acid sequence at least 85% identical to the nucleic acid sequence as set forth in SEQ ID NO: 17 and the third bacteriophage has a genomic nucleic acid sequence at least 85% identical to the nucleic acid sequence as set forth in SEQ ID NO: 21.

According to embodiments of the invention, the first bacteriophage has a genomic nucleic acid sequence at least 85% identical to the nucleic acid sequence as set forth in SEQ ID NO: 17, the second bacteriophage has a genomic nucleic acid sequence at least 85% identical to the nucleic acid sequence as set forth in SEQ ID NO: 19 and the third bacteriophage has a genomic nucleic acid sequence at least 85% identical to the nucleic acid sequence as set forth in SEQ ID NO: 20.

According to embodiments of the invention, the first bacteriophage has a genomic nucleic acid sequence at least 85% identical to the nucleic acid sequence as set forth in SEQ ID NO: 7, the second bacteriophage has a genomic nucleic acid sequence at least 85% identical to the nucleic acid sequence as set forth in SEQ ID NO: 9 and the third bacteriophage has a genomic nucleic acid sequence at least 85% identical to the nucleic acid sequence as set forth in SEQ ID NO: 12.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
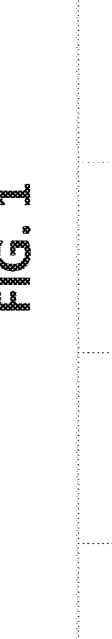
FIG. 1 is a graph illustrating F group single bacteriophage liquid host range targeting Pseudomonas strains (Pst 1-14, 16 and 18-23). 5 µl phage containing solution (bacterial lysate) at concentration $1 \cdot 10^7 - 1 \cdot 10^9$ phages per ml of Ep007 tested with 195 µl of each Pst bacterium at $OD_{600} = 0.3$. The bacteria used was as follows: Pst1-14, 16 and 18-23 (DC). 10 µl of the phage solution was tested with 190 µl of each Pst bacteria at $OD_{600} = 0.3$ in its logarithmic growth stage. Host range was defined by bacterial susceptibility or resistance to tested bacteriophages. Bacteriophage Ep007 from group F inhibited almost all Pst strains growth (except Pst 2, 6, 7, 11, 18 and 19).

The present invention, in some embodiments thereof, relates to agricultural compositions comprising bacteriophages for the control of plant pathogens.

Before explaining at least one embodiment of the invention in detail, it is to be understood that the invention is not necessarily limited in its application to the details set forth in the following description or exemplified by the examples. The invention is capable of other embodiments or of being practiced or carried out in various ways.

The present inventors have uncovered novel bacteriophages that are capable of infecting, replicating within and lysing *Pseudomonas syringae* pv. tomato. The present inventors propose that such bacteriophages are useful in controlling bacterial speck disease in tomato plants.

Whilst reducing the present invention to practice, the present inventors have now uncovered that particular combinations of these novel phages are synergistic in their ability to lyse the bacteria and therefore bring about an enhanced ability to control bacterial speck in plants.

Thus, according to a first aspect of the present invention, a method of controlling or preventing bacterial speck disease is provided by contacting the plant with an effective amount of at least one bacteriophage capable of infecting the plant pathogen *Pseudomonas syringae* pv. tomato, the at least one bacteriophage having a genomic nucleic acid sequence at least 85% identical to the nucleic acid sequence as set forth in SEQ ID NOs: 1, 2, 3, 4, 5, 6, 78, 9, 10, 11, 12, 13, 14, 15, 16, 17, 18, 19, 20, 21, 22 or 23, thereby controlling or preventing the bacterial speck disease of the plant.

The term "plant" as used herein encompasses whole plants, a grafted plant, ancestors and progeny of the plants and plant parts, including seeds, shoots, stems, roots, rootstock, scion, foliage and plant cells, tissues and organs. The plant may be in any form including suspension cultures, embryos, meristematic regions, callus tissue, leaves, gametophytes, sporophytes, pollen, and microspores.

The tomato plant can be of a cultivated genetic background or a wild tomato genetic background.

As used herein, the term "tomato" refers to a plant, line or population within the species *Solanum lycopersicum* (synonyms are *Lycopersicon lycopersicum* or *Lycopersicon esculentum*) or formerly known under the genus name of *Lycopersicon* including but not limited to *L. cerasiforrne, L. cheesmanii, L. chilense, L. chmielewskii, L. esculentum* (now *S. pennellii*), *L. hirsutum, L. parviborum, L. pennellii, L. peruvianum, L. pimpinellifolium*, or *S. lycopersicoides*. The newly proposed scientific name for *L. esculentum* is *S. pennellii*. Similarly, the names of the wild species may be altered. *L. pennellii* has become *S. pennellii, L. hirsutum* may become *S. habrochaites, L. peruvianum* may be split into S. 'N peruvianum' and S. 'Callejon de Hueyles', *S. peruvianum*, and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense*, and *L. pimpinellifolium* may become *S. pimpinellifolium*.

Generally, a cultivated tomato refers to tomato which is suitable for consumption and meets the requirements for commercial cultivation, e.g. typically classified as *Solanum lycopersicum*. In addition to the tomato plants themselves, and the parts thereof suitable for consumption, such as the fruit, the invention comprises parts or derivatives of the plant suitable for propagation. Examples of parts suitable for propagation are organ tissues, such as leaves, stems, roots, shoots and the like, protoplasts, somatic embryos, anthers, petioles, cells in culture and the like. Derivatives suitable for propagation are for instance seeds. The plants according to the invention can be cultivated or propagated in the conventional manner but also by means of tissue culture techniques from plant parts.

The choice of a variety depends on market demand, regional adaptability, disease resistance and the end use of the product. Exemplary segments for fresh market tomatoes include, but are not limited to, Beef (fruit weight of about 220-400 gr), Standard (fruit weight of about 160-220 gr) and Cluster (uniform fruit weight of about 120-180 gr). Such varieties are available from major seed companies e.g., Grodena, Macarena, Estatio, Zouk, Climbo and Climstar, all available from Syngenta. Other varieties can be proprietary or available from other vendors, including but not limited to, Cherry-micro (up to 5 gr) round cherry, mini round cherry (7.5-15 gr), mini plum elongated cherry (10-25 gr). Examples for these varieties are: Creativo (Clause), Batico (Nirit seeds), Shiren (Hazera Genetics). Cocktail round and elongated (25-40 gr): Romanita, Cherry and Cocktail with red, yellow, orange, pink, zebra, chocolate background. Examples include, but are not limited to, Summer sun (Hazera Genetics), Black pearl (Burpee) Tyty (Tomodori). Roma determinate and indeterminate. 120-200 gr. Examples for the intermediate marker include, but are not limited to, lancelot (Vilomorin) and Parsifal (Vilomorin). Pink tomato divided to beef (220-400), standard (160-220) and cluster (120-180). Example: Momotaro type, Cor di bue tomato, (150-350 gr), Pinton (250-300 gr), open field tomato-determinate or semi-determinate (180-400 gr).

Exemplary cultivars of processing tomatoes include, but are not limited to, Roma, SUN 6366, AB 2, Heinz 9780, Heinz 9557, Halley 3155 and Hypeel 303.

There are two major types of tomato growth: determinate and indeterminate. Determinate growth produces "bush" tomatoes and which are bred for compactness. The entire plant stops growing once the terminal fruit ripens, the remainder of the fruit all ripen nearly simultaneously, and then the plant dies. Indeterminate growth produces tomatoes that can grow up to 10 feet in height (so-called "vining"

tomatoes) and will only stop growing when killed (e.g. by frost). Their fruits ripen sequentially. In a typical plant, all growth arises from the reiteration of modular sympodial units that each produce three leaves and a multiflowered inflorescence. Most field-grown varieties of tomato, including M82, are determinate plants whose shoots produce an average of six sympodial units, each harboring a single inflorescence, within which leaf number gradually decreases before a precocious termination of growth. In general, determinate tomatoes are suitable for open field production. Semi-determinate and indeterminate "cultivated" varieties are suitable for staked cultivation in the open field or protected nets and for glasshouse cultivation.

According to an embodiment of the invention the tomato plant is a determinate tomato.

According to an embodiment of the invention the tomato plant is an indeterminate tomato.

According to an embodiment of the invention the tomato plant is a semi-determinate tomato.

According to an embodiment, the tomato is selected from the group consisting of a single fruit per truss, branched tomato and cherry tomato.

As used herein, the term "bacteriophage" and "phage" are used interchangeably and refer to an isolated virus that is capable of infecting a bacterium. Typically, a bacteriophage will be characterized by: 1) the nature of the nucleic acids that make up its genome, e.g., DNA, RNA, single-stranded or double-stranded and/or the genomic sequence thereof; 2) the nature of its infectivity, e.g., lytic or temperate; 3) the receptor on the bacterium to which the bacteriophage is attached during the infection; and 4) the particular bacterial subspecies that it infects (and in certain instances the particular strain of that subspecies). This aspect is known as "host range".

As used herein, the phrases "isolated bacteriophage", "isolate" or grammatical equivalents refer to a bacteriophage which is removed from its natural environment (e.g. removed from bacteria which it typically infects or soil, water and other material in which it dwells). In one embodiment, the isolated bacteriophage is removed from cellular material and/or other elements that naturally exist in the source clinical or environmental sample. The term isolated bacteriophages includes such bacteriophages isolated from the environment ("environmental isolates").

In one embodiment, the bacteriophages are lytic.

The term "lytic bacteriophage" refers to a bacteriophage that infects a bacterial host and causes that host to lyse without incorporating the bacteriophage nucleic acids into the host genome. A lytic bacteriophage is typically not capable of reproducing using the lysogenic cycle.

In another embodiment, the bacteriophages are lysogenic.

The term "lysogenic bacteriophage" refers to a bacteriophage that is capable of reproducing using the lysogenic cycle.

As used herein, the phrase "bacteriophage strain" refers to the sequenced phage, as described herein.

The term "*Pseudomonas syringae* pv. tomato" relates to the gram-negative bacterial pathogen which is the causal agent of bacterial speck of tomato. According to some classifications, it belongs to the species *P. syringae* genospecies III.

Exemplary strains of *Pseudomonas syringae* pv. tomato that are infected by the bacteriophage strains of the present invention are those that are found in environmental specimens (e.g. soil, water and other material).

In a particular embodiment, the bacteriophages described herein are capable of infecting at least one, two, three, four, five, six, seven, eight, nine or more *Pseudomonas syringae* pv. tomato strains that are causative for bacterial speck disease.

Also contemplated are progeny of the bacteriophages that have a genomic nucleic acid as set forth in SEQ ID NOs: 1-23, wherein the progeny is capable of infecting the same subspecies (or even strain) of bacteria as that which the parent bacteriophage having one of the above set forth genomic nucleic acid sequence infects. Such progeny may have genomes having a sequence at least 85% identical, at least 90% identical, at least 91% identical, at least 92% identical, at least 93% identical, at least 94% identical, at least 95% identical, 96% identical, 97% identical 98% identical, or 99% identical to the genome of the parent bacteriophage.

As used herein, the term "or progeny of the bacteriophage" refers to bacteriophages stemming from or derived from the strains identified herein.

Also contemplated are functional homologs of those that have a genomic nucleic acid sequence as set forth in SEQ ID NOs: 1-23 (in particular SEQ ID NOs: 1 1-11, 13-15, 18-20 and 22-23), wherein the functionally homologous bacteriophage is capable of infecting essentially bacteria of the same subspecies (or strain) as that which the bacteriophage having one of the above set forth genomic nucleic acid sequence infects. Typically, the homologs have a genomic nucleic acid sequence at least 85%, 86%, 87%, 88%, 89%, 80%, 91%, 92%, 93%, 94%, 95%, 96%, 97%, 98% 99% identical to the nucleic acid sequences as set forth in SEQ ID NOS: 1-23.

As used herein "functional homolog" or "functionally homologous" or "variant" or grammatical equivalents as used herein refer to a bacteriophage with a genomic nucleic acid sequence different than that of the sequenced bacteriophage (e.g., at least one mutation) resulting in a bacteriophage that is endowed with substantially the same ensemble of biological activities (+/−10%, 20%, 40%, 50%, 60% when tested under the same conditions) as that of the sequenced bacteriophage and can be classified as infecting essentially the same strain or subspecies of bacteria based on known methods of species/strain classifications.

A bacteriophage "infects" bacteria if it is capable of incorporating its nucleic acid into the bacterial cell.

In one embodiment, the viral nucleic acid integrates into the bacterial genome (i.e. lysogenic pathway).

According to a particular embodiment, the bacteriophage disclosed herein lyse their target bacteria.

According to some embodiments, the genomic nucleic acid sequence of the bacteriophages described herein is at least about 85%, at least about 90%, at least about 91%, at least about 92%, at least about 93%, at least about 94%, at least about 95%, at least about 96% least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95% 99.95%, at least about 99.99%, or more identical to the genomic sequence of the genomic sequences as set forth in SEQ ID NOs: 1, 2, 3, 4, 5, 6, 7, 8, 9, 10, 11, 12, 13, 14, 15, 16, 17, 18, 19, 20, 21, 22 or 23.

In particular, the bacteriophage has a genomic nucleic acid sequence at least 95% identical (% homologous) to the nucleic acid sequence as set forth in SEQ ID NOs: 1, 2, 3, 4, 5, 6, 7, 8, 9, 10, 11, 12, 13, 14, 15, 16, 17, 18, 19, 20, 21, 22 or 23.

According to a specific embodiment, the bacteriophage has a genomic nucleic acid sequence at least 95% identical (% homologous) to the full length nucleic acid sequence as set forth in SEQ ID NOs: 1, 2, 3, 4, 5, 6, 7, 8, 9, 10, 11, 12, 13, 14, 15, 16, 17, 18, 19, 20, 21, 22, or 23.

As used herein, "percent homology", "percent identity", "sequence identity" or "identity" or grammatical equivalents as used herein in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89 (22): 10915-9].

Percent identity can be determined using any homology comparison software, including for example, the BLASTN software of the National Center of Biotechnology Information (NCBI) such as by using default parameters.

Other exemplary sequence alignment programs that may be used to determine % homology or identity between two sequences include, but are not limited to, the FASTA package (including rigorous (SSEARCH, LALIGN, GGSEARCH and GLSEARCH) and heuristic (FASTA, FASTX/Y, TFASTX/Y and FASTS/M/F) algorithms, the EMBOSS package (Needle, stretcher, water and matcher), the BLAST programs (including, but not limited to BLASTN, BLASTX, TBLASTX, BLASTP, TBLASTN), megablast, DIAMOND and BLAT. In some embodiments, the sequence alignment program is BLASTN. For example, 95% homology refers to 95% sequence identity determined by BLASTN, by combining all non-overlapping alignment segments (BLAST HSPs), summing their numbers of identical matches and dividing this sum with the length of the shorter sequence.

In some embodiments, the sequence alignment program is a basic local alignment program, e.g., BLAST. In some embodiments, the sequence alignment program is a pairwise global alignment program. In some embodiments, the pairwise global alignment program is used for protein-protein alignments. In some embodiments, the pairwise global alignment program is Needle. In some embodiments, the sequence alignment program is a multiple alignment program. In some embodiments, the multiple alignment program is MAFFT. In some embodiments, the sequence alignment program is a whole genome alignment program. In some embodiments, the whole genome alignment is performed using BLASTN. In some embodiments, BLASTN is utilized without any changes to the default parameters.

According to some embodiments of the invention, the identity is a global identity, i.e., an identity over the entire nucleic acid sequences of the invention and not over portions thereof.

According to an additional or alternative embodiment, a functional homolog is determined as the average nucleotide identity (ANI), which detects the DNA conservation of the core genome (Konstantinidis K and Tiedje J M, 2005, Proc. Natl. Acad. Sci. USA 102:2567-2592). In some embodiments, the ANI between the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is of at least about 95%, at least about, 96%, at least about 97%, at least about 98%, at least about 99%, at least about 99.1%, at least about 99.5%, at least about 99.6%, at least about 99.7%, at least about 99.8%, at least about 99.9% or more.

According to an additional or alternative embodiment, a functional homolog is determined by the degree of relatedness between the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 determined as the Tetranucleotide Signature Frequency Correlation Coefficient, which is based on oligonucleotide frequencies (Bohlin J. et al. 2008, BMC Genomics, 9:104). In some embodiments, the Tetranucleotide Signature Frequency Correlation coefficient between the variant and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22, 23 or 24 is of about 0.99, 0.999 or more.

According to an additional or alternative embodiment, the degree of relatedness between the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is determined as the degree of similarity obtained when analyzing the genomes of the parent and of the variant bacteriophage by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is of at least about 96%, at least about 97%, at least about 98%, at least about 99%, at least about 99.1%, at least about 99.5%, at least about 99.6%, at least about 99.7%, at least about 99.8%, at least about 99.9% or more.

According to an additional or alternative embodiment, the degree of relatedness between the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is determined by the Pearson correlation coefficient obtained by comparing the genetic profiles of both phages obtained by repetitive extragenic palindromic element-based PCR (REP-PCR) (sec e.g. Chou and Wang, Int J Food Microbiol. 2006, 110:135-48). In some embodiments, the Pearson correlation coefficient obtained by comparing the REP-PCR profiles of the variant and the sequenced bacteriophage is of at least about 0.99, at least about 0.999 or more-see for example bmcmicrobioldotbiomedcentraldotcom/articles/10.1186/s12866-020-01770-2 (Damnjanovic et al, BMC Microbiol 20, 154 (2020)).

According to an additional or alternative embodiment, the degree of relatedness between the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is defined by the linkage distance obtained by comparing the genetic profiles of both phages obtained by Multi-locus sequence typing (MLST) (see e.g. Maiden, M. C., 1998, Proc. Natl. Acad. Sci. USA 95:3140-3145). In some embodiments, the linkage distance obtained by MLST of the functional homolog and the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23 is of at least about 0.99, at least about 0.999 or more.

According to an additional or alternative embodiment, the functional homolog comprises a functionally conserved gene or a fragment thereof e.g., an integrase gene, a polymerase gene, a capsid protein assembly gene, a DNA terminase, a tail fiber gene, or a repressor gene that is at least about 97%, at least about 98%, at least about 99%, at least about 99.1%, at least about 99.5%, at least about 99.6%, at least about 99.7%, at least about 99.8%, at least about 99.9%, or more identical to that of the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23.

According to an additional or alternative embodiment, the functional homolog is defined by a comparison of the coding sequence (gene) order.

According to an additional or alternative embodiment, the functional homolog is defined by a comparison of order of non-coding sequences.

According to an additional or alternative embodiment, the functional homolog is defined by a comparison of order of coding and non-coding sequences.

According to some embodiments of the invention, the combined coding region of the functional homolog is such that it maintains the original order of the coding regions as within the genomic sequence of the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23, yet without the non-coding regions.

For example, in case the genomic sequence has the following coding regions, A, B, C, D, E, F, G, each flanked by non-coding sequences (e.g., regulatory elements, and the like), the combined coding region will include a single nucleic acid sequence having the A+B+C+D+E+F+G coding regions combined together while maintaining the original order of their genome, yet without the non-coding sequences.

According to some embodiments of the invention, the combined non-coding region of the functional homolog is such that it maintains the original order of the non-coding regions as within the genomic sequence of the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23, yet without the coding regions as originally present in the original bacteriophage.

According to some embodiments of the invention, the combined non-coding region and coding region (i.e., the genome) of the functional homolog is such that it maintains the original order of the coding and non-coding regions as within the genomic sequence of the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23.

As used herein "maintains" relate to at least about 90%, 91%, 92%, 93%, 94%, 95%, 96%, 97%, 98%, 99% or 100% of the coding and/or non-coding regions of the functional homolog compared to the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23.

According to an additional or alternative embodiment, the functional homolog is defined by a comparison of gene content.

According to a specific embodiment, the functional homolog comprises a combined coding region at least about 90%, at least about 91%, at least about 92%, at least about 93%, at least about 94%, at least about 95%, at least about 96%, at least about 97%, at least about 98%, at least about 99%, or more (e.g., 100%) identical to the combined coding region existing in genome of the bacteriophage having a genome as set forth in any one of SEQ ID NO: 1, 2, 3, 4, 5, 6, 7, 8, 9, 10, 11, 12, 13, 14, 15, 16, 17, 18, 19, 20, 21, 22 or 23.

As used herein "combined coding region" refers to a nucleic acid sequence including all of the coding regions of the original bacteriophage yet without the non-coding regions of the original bacteriophage.

In one embodiment, the bacteriophages show up to 85%, 86%, 87%, 88%, 89%, 90%, 91%, 92%, 93%, 94%, 95%, 96%, 97%, 98%, 99% sequence identity with the bacteriophages disclosed herein and share at least one of the following characteristics-similar host range; similar type of infectivity (i.e., lytic or temperate).

In another embodiment, the bacteriophages show up to 85%, 86%, 87%, 88%, 89%, 90%, 91%, 92%, 93%, 94%, 95%, 96%, 97%, 98%, 99% sequence identity with the bacteriophages disclosed herein and share both of the following characteristics-similar host range, similar type of infectivity.

Additional bioinformatics methods that may be used to determine relatedness between two bacteriophage genomes include Nucmer and Minimap, both of which are alignment based tools; Jacard distance and MinHash, each of which are information based tools; and Codon usage similarity, pathway similarity and protein motif similarity.

As used herein, "host range" refers to the bacteria that are susceptible to infection by a particular phage. The host range of a bacteriophage may include, but is not limited to, a strain, a subspecies, a species, a genus, or multiple genera of bacteria.

Bacteriophage isolates may be prepared and phenotyped using methods known in the art, e.g., a plaque assay, liquid media assay, solid media assay. In some embodiments, the solid media assays to quantify and isolate bacteriophage are based on plaque assays (S. T. Abedon et al., Methods in Molecular Biology 2009 (Clifton, N.J.), 501, 161-74), ranging from efficiency of plating (EOP) (E. Kutter, Methods in Molecular Biology 2009 (Clifton, N.J.), 501, 141-9) to spot testing (P. Hyman et al., Advances in Applied Microbiology (1st ed., Vol. 70, pp. 217-48) 2010. Elsevier Inc.). In some embodiments, the plate format used for the plaque assay can be modified, e.g., from a petri dish to a 48-well plate.

In some embodiments, infectivity is determined by the plaque presence in a solid assay only. In some embodiments, infectivity is determined by the plaque presence in a liquid assay only. In some embodiments, infectivity is determined by the plaque presence in both the liquid assay and the solid assay.

The bacteriophages described herein are typically present in a preparation in which their prevalence (i.e., concentration) is enriched over that (exceeds that) found in nature.

Since bacteriophages infect bacterial cells, they may be found in specimens or samples which are rich in bacteria—e.g. environmental samples such as soil, water and other material. According to some embodiments of the invention, the agricultural composition (i.e. preparation) comprises less than 50 microbial species, e.g., bacteria and/or fungi—e.g. less than 40 bacterial species, less than 30 bacterial species, less than 20 bacterial species, less than 10 bacterial species, less than 5 bacterial species, less than 4 bacterial species, less than 3 bacterial species, less than 2 bacterial species or even devoid completely of bacteria.

According to a particular embodiment, the agricultural composition comprises a single strain of bacteriophage (or a functional homolog thereof), no more than two different bacteriophage strains (or functional homologs thereof), no more than three different bacteriophage strains (or functional homologs thereof), no more than four different bacteriophage strains (or functional homologs thereof), no more than five different bacteriophage strains (or functional homologs thereof), no more than six different bacteriophage strains (or functional homologs thereof), no more than seven different bacteriophage strains (or functional homologs thereof), no more than eight different bacteriophage strains (or functional homologs thereof), no more than nine different bacteriophage strains (or functional homologs thereof), or no more than ten different bacteriophage strains (or functional homologs thereof).

In a particular embodiment, the agricultural composition comprises no additional bacteriophage that infect plant pathogens other than *Pseudomonas syringae* pv. tomato.

In a particular embodiment, the preparation comprises no additional bacteriophage that infects non-plant pathogens (e.g. bacteria that cause disease in humans).

The present inventors contemplate agricultural compositions comprising bacteriophages that are directed only to *Pseudomonas syringae* pv. tomato.

Particular combinations of bacteriophages that are directed to *Pseudomonas syringae* pv. tomato that are contemplated include:

1. SEQ ID NO: 7 and SEQ ID NO: 9;
2. SEQ ID NO: 7 and SEQ ID NO: 17;
3. SEQ ID NO: 7 and SEQ ID NO: 18;
4. SEQ ID NO: 7 and SEQ ID NO: 19;
5. SEQ ID NO: 7 and SEQ ID NO: 12;
6. SEQ ID NO: 12 and SEQ ID NO: 9;
7. SEQ ID NO: 7, SEQ ID NO: 9 and SEQ ID NO: 12;
8. SEQ ID NO: 17 and SEQ ID NO: 18;
9. SEQ ID NO: 17 and SEQ ID NO: 19;
10. SEQ ID NO: 7, SEQ ID NO: 9 and SEQ ID NO: 18;
11. SEQ ID NO: 7, SEQ ID NO: 9 and SEQ ID NO: 19;
12. SEQ ID NO: 17, SEQ ID NO: 18 and SEQ ID NO: 19;
13. SEQ ID NO: 7, SEQ ID NO: 17, SEQ ID NO: 18 and SEQ ID NO: 19.
14. SEQ ID NO: 7, SEQ ID NO: 17 and SEQ ID NO: 21.
15. SEQ ID NO: 17, SEQ ID NO: 19 and SEQ ID NO: 20.

The bacteriophage compositions can be applied to plants by spraying, fogging, dusting, coating, soaking, irrigation, drenching or otherwise treating them with the active ingredients or alternatively, by treating the plant seeds, the soil around the plant, or the soil, rice pads or the water for hydroponic culture where the seeds are to be sown with the bacteriophages. The application may be affected either before (preventatively) or after the plant is infected with the pathogen.

According to an embodiment, the regimen is performed such as to control the spread of the pathogen and/or eliminate the pathogen and/or eliminate/reduce/minimize any damage that can be caused by the pathogen.

The bacteriophages can be formulated as dips, sprays, seed coatings or concentrates.

In one embodiment, the bacteriophages are provided as a dried formulation—e.g. powder.

It will be appreciated that by controlling (i.e. reducing) pathogenic infection in the plant, the post-harvest quality of the plant is improved and losses are reduced. Concurrently, or alternatively, plant performance parameters may also be improved (including, but not limited to growth parameters, crop production, and pathogenic resistance).

The contacting may be effected at any stage of the plant life cycle e.g. a post-blossom stage, a blossom stage, a pre-blossom stage, or any combination thereof.

In one embodiment, the contacting is effected at the seedling stage (e.g. 4 leaf stage)

The contacting may be effected in the vicinity of or onto: a root, a stem, a trunk, a seed, a fruit, a flower, a leaf, or any combination thereof of the plant.

According to an embodiment, applying is in an open field. According to an embodiment, applying is in a greenhouse or a nursery. According to an embodiment, applying is applying once. According to an embodiment, applying is applying at least twice at any regimen or duration.

According to an embodiment, the applying comprises repeated application (2 or more applications e.g., every day, every week, seasonal, bi-weekly, bi-monthly etc.). Repeated applications are especially envisaged for field/greenhouse treatments.

According to an embodiment, repeated application comprises daily, weekly, daily, monthly, or bi-monthly administration during blossom, post-blossom, pre-blossom, or any combination thereof. For example, suggested regimen may include but is not limited to, spraying plants in open fields and green house, adding to irrigation of plants grown in the open field, green house, nursery and in pots.

It has been demonstrated that applying phage to tomato leaves in the evening resulted in longer phage persistence in the phyllosphere, giving phage more time to infect and kill their bacterial targets (Balogh et al., Plant Dis. 87, 949-954. doi: 10.1094/PDIS.2003.87. 8.949, 2003; Iriarte et al., Appl. Environ. Microbiol. 73, 1704-1711. doi: 10.1128/AEM.02118-06, 2007).

Accordingly, in one embodiment, the contacting is not carried out during daylight hours In one embodiment, the contacting is effected in the absence of a copper based product.

The bacteriophages disclosed herein may be provided per se, or may be formulated with an agriculturally acceptable carrier.

As used herein the term "agriculturally acceptable carrier" refers to a material that facilitates application of the bacteriophage to the intended target, which may be for example a plant, a plant material, compost, earth, surroundings or equipment, or that facilitates storage, transport or handling. Carriers used in compositions for application to plants and plant material are preferably non-phytotoxic or only mildly phytotoxic. A suitable carrier may be a solid, liquid or gas depending on the desired formulation. In one embodiment the carriers include polar liquid carriers such as water, mineral oils and vegetable oils. In one embodiment the carrier enhances the stability of the active ingredient as described herein.

The carrier can include a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof. One of ordinary skill in the art can readily determine the appropriate carrier to be used taking into consideration factors such as a particular bacteriophage strain, plant to which the bacteriophage is to be applied, type of soil, climate conditions, whether the bacteriophage is in liquid, solid or powder form, and the like.

The additive can comprise an oil, a gum, a resin, a clay, a poly ethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof.

The surfactant can contain a heavy petroleum oil, a heavy petroleum distillate, a polyol fatty acid ester, a polyethoxylated fatty acid ester, an aryl alkyl poly ethylene glycol, an alkyl amine acetate, an alkyl aryl sulfonate, a polyhydric alcohol, an alkyl phosphate, or a combination thereof.

The anti-caking agent can include a sodium salt such as a sodium sulfite, a sodium sulfate, a sodium salt of monomethyl naphthalene sulfonate, a sodium salt of dimethyl naphthalene sulfonate, or a combination thereof; or a calcium salt such as calcium carbonate, diatomaceous earth, or a combination thereof.

In one embodiment, the composition is devoid of copper based element.

Exemplary agriculturally acceptable carriers include, but are not limited to, vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

The bacteriophage cultures can be prepared as solid, liquid. emulsion or powdered formulations as is known in the art. The cultures of the present invention can be formulated as a seed coating formulation, a liquid formulation for application to plants or to a plant growth medium, or a solid formulation for application to plants or to a plant growth medium.

When the bacteriophage culture is prepared as a liquid formulation for application to plants or to a plant growth medium, it can be prepared in a concentrated formulation or a working form formulation. In some instances, the seed coating formulation of the present invention is an aqueous or oil-based solution for application to seeds.

When the bacteriophage culture of the present invention is prepared as a solid formulation for application to plants or to a plant growth medium, it can be prepared as a granular formulation or a powder agent. The seed coating formulation can be a powder or granular formulation for application to seeds.

The bacteriophage culture can further include an agrochemical (i.e. an agent that promotes the growth of a plant and/or maintains the health of a plant).

Examples of such agents include a fertilizer, a micronutrient fertilizer material, an insecticide, a herbicide, a plant growth regulator, an acaricide, a rodenticide, a fungicide, a nutrient, a molluscicide, an algicide, a pesticide, a fungal inoculant, or a combination thereof.

In some instances, the fertilizer is a liquid fertilizer. The agrochemical can either be applied to a plant growth medium or to plants and/or seeds. Liquid fertilizer can include, without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archacosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

In one embodiment, the plant growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic c acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole. Other examples of plant growth regulators which can be comprised in the article of manufacture include those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Other plant growth regulators that can be incorporated seed coating compositions are described in US 2012/0108431, which is incorporated by reference in its entirety.

Preferred nematode-antagonistic biocontrol agents include ARF18; *Arthrobotrys* spp.; *Chactomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paccilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora*, *Arthrobotrys dactyloides*, *Chactomium globosum*, *Cylindrocarpon heteronema*, *Exophilia jeanselmei*, *Exophilia pisciphila*, *Fusarium aspergilus*, *Fusarium solani*, *Gliocladium catenulatum*, *Gliocladium roseum*, *Gliocladium vixens*, *Hirsutella rhossiliensis*, *Hirsutella minnesotensis*, *Lecanicillium lecanii*, *Monacrosporium drechsleri*, *Monacrosporium gephyropagum*, *Myrotchcium verrucaria*, *Neocosmospora vasinfecta*, *Paccilomyces lilacinus*, *Pochonia chlamydosporia*, *Stagonospora heteroderac*, *Stagonospora phascoli*, vesicular-arbuscular mycorrhizal fungi, *Burkholderia cepacia*, *Pasteuria penetrans*, *Pasteuria thornei*, *Pasteuria nishizawae*, *Pasteuria ramosa*, *Pastrucia usage*, *Brevibacillus laterosporus* strain G4, *Pseudomonas fluorescens* and *Rhizobacteria*.

In another embodiment, the bacteriophage preparation can comprise a nutrient. The nutrient can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

In one embodiment, the preparation may comprise a rodenticide selected from the group of substances consisting of 2-isovalerylindan-1,3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Phage Isolation from Environmental Sample

Materials And Methods

Isolation of bacteriophages from environmental samples: Soil samples were collected from open fields and greenhouses where tomato plants are grown or were grown recently. Samples were collected from 20-30 positions within the same location and pooled into 3-6 pools per location. Samples were typically derived from the root-associated soil, at shallow depth of up to 20 cm.

For bacteriophage isolation, 5-10 gr of pooled soil samples, were mixed with 25 ml of Nutrient Broth (NB) in the presence of 100 µg/ml cycloheximide and 100 µl of an overnight culture of the target bacterium. In each isolation experiment, one strain of the target bacteria was added to the mixture.

Mixtures containing soil samples, growth media, antibiotics and bacteria were shaken for 18-24 hours at 200 RPM, at 27° C. Then the mixtures were centrifuged for 10 minutes at 4,000 RCF, the supernatant was filtered through 2 layers of gauze and centrifuged again for 5 minutes at 4,000 RCF. The supernatant was then filtered through 0.45 µm filter and the sterile liquid (lysate with the phages) was collected in a fresh tube for further analysis.

Overlay plaque assay: An overnight culture of the same target bacterial strain that was used for bacteriophage isolation, was diluted to $OD_{600}=0.1$ and was grown for several hours until the $OD_{600}$ reached 0.3, suggesting early logarithmic (log) phase. 100 µl of the log phase bacteria were mixed with 100 µl of the bacteriophage lysate and left at room temperature for 5 minutes. Next, 4 ml of molten nutrient broth containing 0.5% agar and pre-heated to 55° C., was added to the bacteria/lysate mixture, mixed gently and quickly poured on top of a petri plate containing nutrient agar. The plates were incubated at 27° C. overnight. Plaques were visible as clear circles resulted from bacterial lysis.

Example 2

Phage DNA Extraction and Genome Sequencing

Materials and Methods

DNA extraction: Phages were enriched, each on specific bacterium according to their host range and filtered through a 0.22 µm mesh, this liquid is called a lysate. From each unique lysate, 500 µl were transferred to a clean 1.5 ml microcentrifuge tube and was added 1 µl of 10 mg/ml DNaseI (Sigma) and incubated at 37° C. for one hour. The DNA-free-lysate was further processed using the Qiagen DNA extraction kit Dneasy Blood & Tissue kit (20-69504) according to the product's guidelines for gram positive bacteria.

Sequencing library preparation: DNA sequencing was preformed using the Illumina platform. Library construction was performed using a protocol previously published by Baym et al.[1]. In short, the DNA extractions were quantified using the Qubit HS DNA quantification kit on a Quantus™ device (Promega). 1.5 ng of DNA (1.5 µg/µl) were distributed in one microliter of each sample and were subject to a "Tagmentation" process by mixing TD buffer (15027866) and TDE1 enzyme (15027865) with nucleic acids. This step was followed by the amplification of the tagged fragments, using Kapa Hifi enzyme and buffer alongside a set of sample specific primers called barcodes which enable post-processing of sequences according to source sample.

After the amplification step the libraries were cleaned and a size selection was performed using the AMPure XP magnetic beads (Beckman Coulter) according to the manufacturer's instruction. The samples were than assessed for average fragment size and quantity using the 4200 TapeStation system (Agilent). High quality samples were sequenced using Illumina system.

Sequence analysis: Quality for the short reads were checked using Fastp and assembled using Unicycler. The resulting assemblies were annotated using Prokka. Assemblies' nucleotides were used to build a Basic Local Alignment Search Tool (BLAST by NCBI) database and were searched against each other in a reciprocal manner. Further, assemblies which were of 95% similarity were clustered to groups and within group diversity was estimated by phylogenetic similarities. This was done by a phylogenetic tree, based on the genome of the analyzed data set. The alignment file of genomes was used to identify the single nucleotide polymorphisms (SNPs), using a multiple sequence alignment program (MAFFT). Phylogenetic reconstruction from genomes was conducted to compare the clustering of isolates against lineage generating approximately-maximum-likelihood phylogenetic tree (FastTree v2.1). Once classifying phylogroups, primer sets were designed to identify the isolates based on the sequence of the representing phage. All primers were tested for specificity within internal bacteriophage repository.

Homology analysis: Genomic sequences of all isolated phages were assembled using SPAde. The sequences were then compared to NCBI's non-redundant nucleotide collection using the BLASTN suite.

Results

The obtained sequences were assembled into genomes (Table 1). These bacteriophage genomes clustered to groups (uppercase letters) according to their genetic similarity, based on whole sequence identity. Several types (subgroups) within each group were also identified (in parentheses of Table 1, column 1).

Sequence analysis included annotation and illustration of main groups. All phages within a group have more than 95% similarity.

TABLE 1

| Phage grouping by sequence similarity | Phage name | SEQ ID | Bacterial host | Average genome size (bp) |
|---|---|---|---|---|
| F(1a) | Ep001 | 1 | Pst | 41379 |
| F(1b) | Ep002 | 2 | Pst | 41402 |
| F(2a) | Ep003 | 3 | Pst | 41361 |
| F(2b) | Ep004 | 4 | Pst | 40804 |
| F(2c) | Ep005 | 5 | Pst | 41367 |
| F(2d) | Ep006 | 6 | Pst | 41379 |
| F(2e) | Ep007 | 7 | Pst | 41364 |
| F(3) | Ep008 | 8 | Pst | 41331 |
| G | Ep009 | 9 | Pst | 41413 |
| G(1) | Ep010 | 10 | Pst | 39587 |
| G(2) | Ep011 | 11 | Pst | 39800 |
| H | Ep012 | 12 | Pst | 42526 |
| I(1) | Ep013 | 13 | Pst | 76208 |
| I(2) | Ep014 | 14 | Pst | 76086 |
| I(3) | Ep015 | 15 | Pst | 76141 |
| J | Ep016 | 16 | Pst | 43277 |
| KB1 | Ep017 | 17 | Pst | 40570 |
| KB16 | Ep019 | 18 | Pst | 40543 |
| AY2 | Ep020 | 19 | Pst | 98129 |
| SH1 | Ep021 | 20 | Pst | 42630 |
| SH2 | Ep022 | 21 | Pst | 40665 |
| SH5 | Ep023 | 22 | Pst | 40917 |
| SH8 | Ep024 | 23 | Pst | 39193 |

The primers were designed for each of the main groups for quality control purposes and are set forth in Table 2.

TABLE 2

| Target group | Product size | Forward | Reverse | Target gene/s |
|---|---|---|---|---|
| G (Ep009) | 330 | TGTACAGTTGAGGACC ACGC (SEQ ID NO: 25) | GGCGATGTCGTAATGG CAAC (SEQ ID NO: 26) | DNA packaging-> Holin |
| H (Ep012) | 187 | CGAACAGGCGATAGC AAAGC (SEQ ID NO: 27) | CCTTGCGTAAGCCGCA ATAC (SEQ ID NO: 28) | Non coding between tail proteins |
| F (Ep007) | 774 | ATTGGTCGCGGGGTTT ACTT (SEQ ID NO: 29) | CGCGCCAGAGTTCTCA TAGT (SEQ ID NO: 30) | DNA polymerase |
| AY2 (Ep020) | 344 | TGACGTTCGCATGGTT GAGA (SEQ ID NO: 31) | CGTTCCCGTTCTTGTC CTCA (SEQ ID NO: 32) | DNA polymerase |
| KB1 (Ep017) | 323 | TGCGTTGAACCAAGCA CAAG (SEQ ID NO: 33) | CAGAGGTCTGACTCGC AGTG (SEQ ID NO: 34) | Tail fiber protein |
| SH1 (Ep021) | 541 | CCAGGGTATTGTGCCA GGAG (SEQ ID NO: 35) | CGTGCAGGTTAGCTCT GTGA (SEQ ID NO: 36) | Putative phage tail tubular protein B |

TABLE 2-continued

| Target group | Product size | Forward | Reverse | Target gene/s |
|---|---|---|---|---|
| SH2 (Ep022) | 369 | ATGAACTGGCTCCAGA AGGC (SEQ ID NO: 37) | CGGTATGGTGCCGAAG CTAT (SEQ ID NO: 38) | Tail fiber protein |
| SH5 (Ep023) | 478 | ACAGCGATCCAAACG ACCAT (SEQ ID NO: 39) | TCTGAGCGTTCTCGCT TTGT (SEQ ID NO: 40) | Tail fiber protein |
| SH8 (Ep024) | 399 | ATCGGAACCTGAACAC TCGG (SEQ ID NO: 41) | CGAGGTAACCTTCAGG AGCC (SEQ ID NO: 24) | Tail fiber protein |

Single plaques were isolated by touching the plaque with a sterile tip, then resuspending in 1 ml NB and repeating the plaque overlay assay two more times as described above. At this point, plaques were considered to present a single bacteriophage and were propagated in 3 ml of NB in the presence of the target bacterium. Lysates were filter-sterilized and the bacteriophage titer was determined using a series of dilutions. DNA was extracted from the phages using the DNeasy Blood & Tissue Kit, Cat. No. 69504 (Qiagen, Germany), performing a DNAse I treatment step prior to the kit's protocol. The DNA was then sequenced using the Illumina Tagment DNA Enzyme and Buffer Kit (Illumina, USA).

For each of the phages, the highest percent identity and coverage is presented in Table 3, herein below.

TABLE 3

| Query phage | Reference (as described in the NCBI repository) | Percent identity | Alignment length | Coverage (% of query) | Mismatch | e value | Bitscore |
|---|---|---|---|---|---|---|---|
| Ep001 | gi\|966198107\|ref\|NC_028661.1\| *Pseudomonas* phage PPPL-1, complete genome | 77.208 | 5322 | 55 | 993 | 0 | 2905 |
| Ep002 | gi\|966198107\|ref\|NC_028661.1\| *Pseudomonas* phage PPPL-1, complete genome | 77.137 | 5323 | 54 | 995 | 0 | 2883 |
| Ep003 | gi\|966198107\|ref\|NC_028661.1\| *Pseudomonas* phage PPPL-1, complete genome | 77.404 | 5200 | 52 | 970 | 0 | 2904 |
| Ep004 | gi\|966198107\|ref\|NC_028661.1\| *Pseudomonas* phage PPPL-1, complete genome | 77.473 | 5207 | 53 | 954 | 0 | 2915 |
| Ep005 | gi\|966198107\|ref\|NC_028661.1\| *Pseudomonas* phage PPPL-1, complete genome | 79.591 | 3910 | 50 | 660 | 0 | 2673 |
| Ep006 | gi\|966198107\|ref\|NC_028661.1\| *Pseudomonas* phage PPPL-1, complete genome | 77.242 | 5330 | 55 | 977 | 0 | 2905 |
| Ep007 | gi\|966198107\|ref\|NC_028661.1\| *Pseudomonas* phage PPPL-1, complete genome | 77.488 | 5206 | 55 | 955 | 0 | 2920 |
| Ep008 | gi\|966198107\|ref\|NC_028661.1\| *Pseudomonas* phage PPPL-1, complete genome | 77.076 | 5322 | 51 | 1000 | 0 | 2867 |
| Ep009 | gi\|966198107\|ref\|NC_028661.1\| *Pseudomonas* phage PPPL-1, complete genome | 78.084 | 16308 | 78 | 3120 | 0 | 9897 |
| Ep010 | gi\|966198107\|ref\|NC_028661.1\| *Pseudomonas* phage PPPL-1, complete genome | 78.084 | 16308 | 79 | 3120 | 0 | 9897 |
| Ep011 | gi\|966198107\|ref\|NC_028661.1\| *Pseudomonas* phage PPPL-1, complete genome | 78.084 | 16308 | 78 | 3120 | 0 | 9897 |
| Ep012 | gi\|971766223\|ref\|NC_029019.1\| *Stenotrophomonas* phage vB_SmaS-DLP_2, complete genome | 97.844 | 22353 | 97 | 445 | 0 | 38573 |
| Ep013 | gi\|589889317\|ref\|NC_023556.1\| *Achromobacter* phage JWAlpha, complete genome | 76.181 | 995 | 2 | 217 | 4.41E−140 | 507 |
| Ep014 | gi\|589889317\|ref\|NC_023556.1\| *Achromobacter* phage JWAlpha, complete genome | 76.281 | 995 | 2 | 216 | 9.46E−142 | 512 |
| Ep015 | gi\|1211142923\|ref\|NC_031062.2\| *Erwinia* phage vB_EamP_Frozen, complete genome | 75.379 | 1320 | 2 | 290 | 1.52E−169 | 604 |
| Ep016 | gi\|971751647\|ref\|NC_028879.1\| *Pseudomonas* phage PaMx42, complete genome | 94.206 | 17120 | 96 | 868 | 0 | 26005 |
| Ep017 | gi\|29366701\|ref\|NC_004665.1\| *Pseudomonas* phage gh-1, complete genome | 97.681 | 22342 | 89 | 494 | 0 | 38367 |
| Ep019 | gi\|966198107\|ref\|NC_028661.1\| *Pseudomonas* phage PPPL-1, complete genome | 77.099 | 5323 | 53 | 997 | 0 | 2872 |
| Ep020 | gi\|589287214\|ref\|NC_023601.1\| *Pseudomonas* phage phiPsa374, complete genome | 83.271 | 10933 | 31 | 1670 | 0 | 9910 |
| Ep021 | gi\|281306659\|ref\|NC_013638.1\| *Pseudomonas* phage phi-2, complete genome | 74.703 | 1601 | 9 | 353 | 0 | 665 |
| Ep022 | gi\|658310745\|ref\|NC_024362.1\| *Pseudomonas* phage phiPSA2, complete genome | 98.391 | 28891 | 96 | 460 | 0 | 50771 |
| Ep023 | gi\|966198107\|ref\|NC_028661.1\| *Pseudomonas* phage PPPL-1, complete genome | 83.621 | 1044 | 15 | 158 | 0 | 968 |
| Ep024 | gi\|844383143\|ref\|NC_027292.1\| *Pseudomonas* phage Pf-10, complete genome | 78.174 | 6955 | 77 | 1317 | 0 | 4248 |

25

Example 3

Host Range Analysis of Phages Targeting *Pseudomonas* Strains

The *Pseudomonas* strains used in the host range analysis are summarized in Table 4, herein below.

TABLE 4

| Country of isolation | Commercial source | Stain | Vendors cat name/number |
|---|---|---|---|
| Denmark | NCPPB | Pst1 | 269 |
| Yugoslavia | NCPPB | Pst2 | 878 |
| Canada | NCPPB | Pst3 | 996 |
| USA | NCPPB | Pst4 | 1008 |
| UK | NCPPB | Pst5 | 1106 |
| Canada | NCPPB | Pst6 | 1368 |
| Switzerland | NCPPB | Pst7 | 2424 |
| New Zealand | NCPPB | Pst8 | 2683 |
| France | NCPPB | Pst9 | 3333 |
| Brazil | NCPPB | Pst10 | 3645 |
| Ukraine | NCPPB | Pst11 | 3784 |
| USA | NCPPB | Pst12 | 4369 |
| UK | ATCC | Pst13 | BAA-871 |
| USA | ATCC | Pst14 | 10862 |
| USA (Cornell University, NY) | NRRL (The Agriculture research service Culture Collection), USA | Pst16 | B-883 |
| JAPAN (IBARAKI) | NARO (National Agriculture and Food Research Organization), Japan | Pst18 | 302665 |
| JAPAN (TOCHIGI) | NARO (National Agriculture and Food Research Organization), Japan | Pst19 | 301591 |
| United States ([Unknown]) | The ICMP (International Collection of Microorganisms from Plants), NZ | Pst20 | ICMP 9324 |
| United Kingdom [Unknown] | The ICMP (International Collection of Microorganisms from Plants), NZ | Pst21 | ICMP 4933 |
| United States (San Diego, California) | The ICMP (International Collection of Microorganisms from Plants), NZ | Pst22 | ICMP 9499 |
| United States | The ICMP (International Collection of Microorganisms from Plants), NZ | Pst23 | ICMP 2843 |
| NSW, Australia | NSW Plant pathology & Mycology Herbarium | Pst24 | DAR 75965 |

26

Host range analysis of each of the isolated phages number 1-24 was performed against bacterial strains number Pst 1-15, 16 and 18-24. (Table 5). The assay was performed by adding a 10 µl drop of each bacteriophage lysate to a plate containing lawn of single bacterial strain. Plates with bacterial lawn and their respective phages were incubated overnight at 27° C. After incubation plaques become visible as a clearing of the bacterial lawn.

TABLE 5

| Phage\Bacteria | Pst 1 | Pst 2 | Pst 3 | Pst 4 | Pst 5 | Pst 6 | Pst 7 | Pst 8 | Pst 9 | Pst 10 | Pst 11 | Pst 12 | Pst 13 | Pst 14 | Pst 15 | Pst 16 | Pst 18 | Pst 19 | Pst 20 | Pst 21 | Pst 22 | Pst 23 | Pst 24 |
|---|---|---|---|---|---|---|---|---|---|---|---|---|---|---|---|---|---|---|---|---|---|---|---|
| Ep007 | + | − | + | + | + | + | + | + | + | + | − | + | + | + | + | + | + | + | + | − | + | + | − |
| Ep020 | + | − | + | − | + | − | − | − | − | − | + | + | + | + | − | − | − | + | + | + | + | + | + |
| Ep017 | − | + | − | − | + | − | + | − | + | + | + | + | + | − | + | + | + | + | + | + | + | − | + |
| Ep019 | + | + | + | + | + | − | + | + | + | + | + | + | + | + | + | + | + | + | + | + | + | + | − |
| Ep021 | − | − | − | − | − | + | + | − | − | − | − | − | − | − | − | − | − | − | − | − | − | − | − |
| Ep022 | − | − | − | − | + | − | + | − | − | − | + | + | + | − | − | − | + | − | + | + | + | − | − |
| Ep023 | − | − | − | − | − | + | + | − | − | − | − | − | − | − | − | − | − | − | − | − | − | − | − |
| Ep024 | − | + | − | − | + | − | − | − | − | − | + | + | − | + | − | − | + | − | + | − | − | − | − |
| Ep001 | + | − | + | + | + | − | + | + | + | + | + |  | + | + |  |  |  |  |  |  |  |  |  |
| Ep002 | + | − | + | + | + | − | + | + | + | + | + |  | + | + |  |  |  |  |  |  |  |  |  |
| Ep003 | + | − | + | + | + | − | + | + | + | + | + |  | + | + |  |  |  |  |  |  |  |  |  |
| Ep004 | − | − | − | − | − | − | − | − | − | − | − |  | + | − |  |  |  |  |  |  |  |  |  |
| Ep005 | + | − | + | + | + | − | + | + | + | − |  |  | + | + |  |  |  |  |  |  |  |  |  |
| Ep006 | + | − | + | + | + | − | + | + | + | + | + |  | + | + |  |  |  |  |  |  |  |  |  |
| Ep008 | + | − | + | − | + | − | + | + | + | − | − |  | + | + |  |  |  |  |  |  |  |  |  |
| Ep009 | − | − | − | + | + | − | + | − | − | + | + |  | + | − |  |  |  |  |  |  |  |  |  |
| Ep010 | − | − | − | − | − | − | − | − | − | − | + |  | + | − |  |  |  |  |  |  |  |  |  |
| Ep011 | − | − | − | − | − | + | − | − | + | − |  |  | − | − |  |  |  |  |  |  |  |  |  |
| Ep012 | − | + | − | − | − | − | − | − | − | + |  |  | − | + |  |  |  |  |  |  |  |  |  |
| Ep013 | − | − | + | − | − | − | − | − | − | − |  |  | − | − |  |  |  |  |  |  |  |  |  |
| Ep014 | − | − | + | − | − | − | − | − | − | − |  |  | − | − |  |  |  |  |  |  |  |  |  |
| Ep015 | − | − | + | − | − | − | − | − | − | − |  |  | − | − |  |  |  |  |  |  |  |  |  |
| Ep016 | − | + | + | − | − | − | − | − | − | − |  |  | − | − |  |  |  |  |  |  |  |  |  |

(+) indicates lysis of the bacterial strain by the isolated phage.

Example 4

Culture Conditions and Synergistic Activity Of Bacteriophage Combinations (Cocktails)

Materials and Methods

In order to examine activity of isolated phages or bacteriophage combinations (cocktails), different strains and species of pathogenic Pseudomonas bacteria were incubated with single phages or combinations of phages. Bacteria were isolated on 1.5% Nutrient Agar (NA) plates by streaking bacterium of interest from frozen 25% glycerol stocks on a 90 mm round NA plate using sterile inoculation loop. Plates were incubated over-night until individual colonies are visible and examined for purity. Using a sterile loop, a single bacterial colony was transferred from a bacterial stock plate into a 15 ml polypropylene culture tube filled with 5 ml of Nutrient Broth (NB). Tubes were vortexed and incubated over-night at 27° C. in shaking incubator set to 180 rpm. A similar tube was used without inoculation as negative control and as blank sample for Optical Density (OD) measurements. Over-night cultures were diluted to $OD_{600}$=0.1, then grown in shaking incubator until $OD_{600}$=0.3, which represents approximately $10^8$ Colony Forming Units (CFU) per ml, at the logarithmic growth stage. 96 wells plate was used for growth curve assays. Each bacteriophage within cocktail was mixed in a similar amount of bacteriophage particles or Plaque Forming Units (PFU) to establish a consistent Multiplicity Of Infection (MOI) against the bacteria. Positive controls included 200 ul bacteria. Negative controls included bacteriophage lysate without bacteria and 200 μl of NB. All samples (phage treatment and control) were performed in triplicates. Plates were inserted to a 800TS Microplate Reader using GENE5 software (BioTek, USA) and were incubated in plate reader at 27° C. for 24 hours run with continuous shaking set of 180 rpm. $OD_{600}$ levels were examined every 15 minutes. At the end of the run, data was extracted to Excel and analyzed for growth inhibition of treated bacteria. Bacteriophage groups F, G, H, I and J were tested with 14 *Pseudomonas syringe* pv. tomato (Pst) strains, internally named Pst 1-14. Host range profile was defined by examining all isolated phages activity on all target bacterial strains. Subsequently, combinations of phages were examined to reveal phages synergy while optimizing maximum pathogen bacterial host range. Most lethal combinations which covered the widest host range were chosen as representative cocktails for in-vitro and in-planta experiments.

Results

Figure 2:
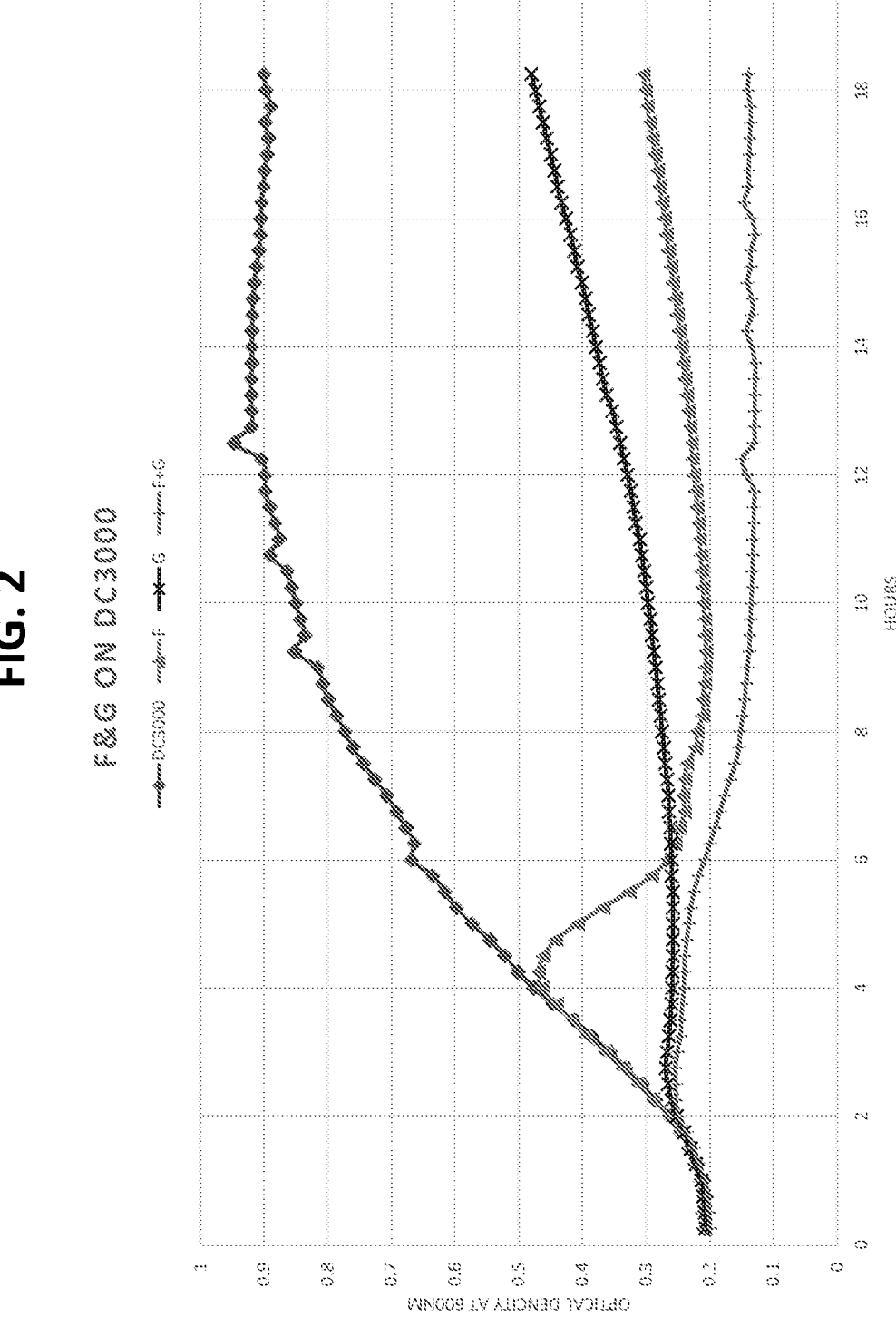
FIG. 2 is a graph illustrating synergistic activity of phages EP007 and EP009 (group F and G representatives) targeting Pst13. Activity of phages EP007 (F) and EP009 (G) against bacterial strain Pst13 was measured for each bacteriophage individually and by combining the two phages. A culture of bacterial strain Pst13 at its logarithmic growth stage was diluted to $OD_{600}=0.3$, and 180 μl of the diluted culture were applied to each well. Each well was then supplemented with 20 μl of one of the phages or a combination of both phages. Double bacteriophage cocktail (F+G) shows lethal and immediate effect on target bacterium with no resistance development within the 18 hours tested.

*Pseudomonas* phages: Phages from F group (infecting pseudomonas bacteria, FIG. 1), exhibited the widest host range in comparison to other phages. Bacteriophage Ep007 inhibited growth of almost all Pst strains (except Pst 2, 7 and 11). Bacteriophage group G, inhibited Pst 7 and 11, and bacteriophage group H inhibited Pst 2. The combination of the phages from groups F, G and H covers the full host range of the pseudomonas bacteria from the EcoPhage library. The synergistic activity of phages EP008 (group F) and EP009 (group G) is illustrated in FIG. 2.

Example 5

Phage Cocktail Protection and Prevention Studies in Plants

Materials and Methods

*Pseudomonas syringae* pv. tomato bacteria were grown in Nutrient Broth (NB) medium and Nutrient Agar that were prepared according to manufacturer recommendations. All cultures were grown at 27° C.

Assessment of Disease Symptoms Inhibition in Tomato Plants

Tomato (*S. lycopersicum*) cv. 4107 seedlings (Yarok2000) were transferred to plastic pots (7*7*8.5 cm, 1 seedling per pot) filled with a commercial soil mixture (HR2 and agrimix). Plants were grown under long-day (16 h light) conditions, at 25° C. and were used for inoculation after developing three-four fully expanded leaves.

One day prior to the start of the experiment, the bacterium (*Pseudomonas*) was grown in liquid NB at 27° C. whilst shaking (180 rpm). On the day of the experiment, bacteria were centrifuged, washed from NB, and resuspended in new NB to reach an $OD_{600}$=0.6 (~$10^{10}$ PFU/ml) in a solution containing $MgCl_2$ and Silwet L-77 in sterile distilled water (DW). Bacterial concentrations were verified by CFU test.

For bacteriophage inoculation, a cocktail composed of 1:1 ratio of each bacteriophage (~$10^9$ PFU/ml) was mixed and diluted 1:10 in bacteriophage solution containing appropriate sugars, in sterile DW. Bacteriophages titer was verified by PFU tests.

The plants' foliage was submerged for 5-10 seconds in bacteriophage solution with bacteriophage cocktails (treatment) or bacteriophage solution without bacteriophage cocktail (control) and left to fully dry (~1-2 h). Plants were then sprayed on both sides of the leaves with bacteria solution by spraying, until slight runoff. For a double bacteriophage treatment, plants were additionally sprayed on both sides of the leaves with bacteriophage cocktail solution until slight runoff. All plants were left to fully dry for about 1-2 hr and transferred to a growth chamber at 25° C. with long-day (16 h light) conditions covered by plastic lids to increase humidity for 48 h.

Disease severity in each leaflet was determined every two to three days after the appearance of disease symptoms (5-6 days post-inoculation) using the following scale: 0—healthy leaflet; 1—less than 10 dark spots; 2—between 10—30 dark spots; 3—over 30 spots without yellowing or browning; 4—over 30 spots with slight yellowing or browning; 5—over 30 spots with significant browning/necrosis that covers less than 50% of the leaflet; 6—over 30 spots with significant browning/necrosis that covers more than 50% of the leaflet; 7—more than 90% of the leaflet is necrotic. In each experiment, each treatment was applied on 5 plants.

Disease inhibition percentage was calculated as:

$$100 - \left( \frac{\text{disease index of treatment}}{\text{disease index of control}} \times 100 \right)$$

Assessment of bacteriophages possible phytotoxic effect was performed by following the appearance of symptoms in plants that were dipped in the bacteriophage cocktail, left to dry, and then sprayed with 10 mM $MgCl_2$ with 0.025% (v/v) Silwet L-77 without bacteria. In each experiment, each control treatment was applied on 3 plants.

Results

Figure 3A:
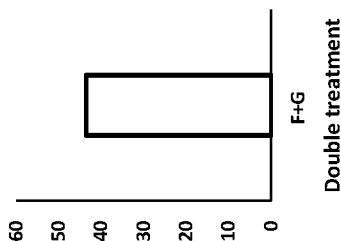
FIGS. 3A-B. Bacterial Speck prevention using bacteriophage cocktails treatment in the tomato-Pseudomonas pathosystems. A—Cocktail of phages EP007 (F) and EP009 (G) targeting bacterial strain Pst5 was examined. Plants foliage were submerged in bacteriophage solution with either bacteriophage cocktail (phages EP007 (F) and EP009 (G)) solutions or experimental solution without bacteriophage cocktail (control), then inoculated with bacteria. Left panel: disease index as determined according to disease severity scale. Right panel: disease inhibition percentage relative to control. Bacteriophage treatment showed approximately 40% disease inhibition. B—Images of representative leaves of plants treated with bacteriophage cocktails or bacterial control were taken 12 days post inoculation. These results show bacterial symptoms were significantly reduced as a result of bacteriophage cocktail treatment.
Figure 3A:
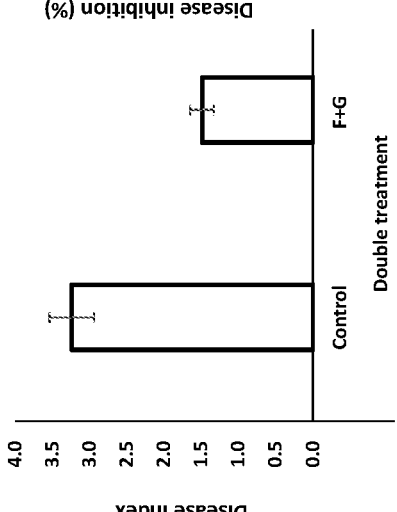
Figure 3B:
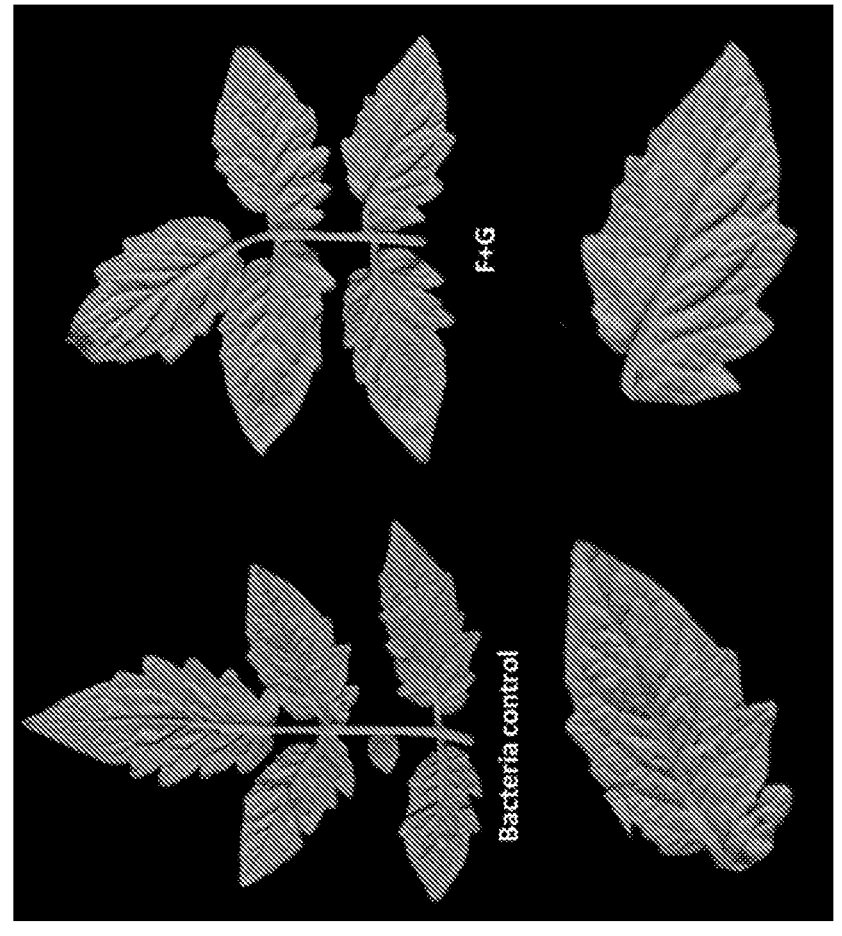

The results illustrated in FIGS. 3A-B demonstrate that treating tomato leaves with a combination of bacteriophage EP007, EP009 and bacteriophage EP012 (groups F, G and H) can significantly reduce the symptoms of the bacterial speck disease caused by the Pseudomonas bacteria.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

SEQUENCE LISTING

The patent contains a lengthy sequence listing. A copy of the sequence listing is available in electronic form from the USPTO web site (https://seqdata.uspto.gov/docdetail?docId=US12593850B2). An electronic copy of the sequence listing will also be available from the USPTO upon request and payment of the fee set forth in 37 CFR 1.19(b)(3).

What is claimed is:

1. An agricultural composition comprising:
   (i) at least three non-identical isolated bacteriophages capable of infecting the plant pathogen *Pseudomonas syringae* pv. tomato, said at least three non-identical bacteriophages having the genomic nucleic acid sequences as set forth in SEQ ID NOs: 17, 19, and 21 respectively; and
   (ii) an agriculturally acceptable carrier, wherein the composition comprises no more than 10 different strains of bacteriophage.

2. The agricultural composition of claim 1, wherein the composition comprises no additional bacteriophage that infects plant pathogens other than *Pseudomonas syringae* pv. tomato.

3. The agricultural composition of claim 1, further comprising an agent which promotes the growth of a plant or maintains the health of the plant.

4. The agricultural composition of claim 3, wherein said agent is selected from the group consisting of a fertilizer, an acaricide, a herbicide, a fungicide, an insecticide, a nematicide, a pesticide, a plant growth regulator, a rodenticide and a nutrient.

5. The agricultural composition of claim 1, wherein said agriculturally acceptable carrier comprises at least one agent selected from the group consisting of a stabilizer, a tackifier, a preservative, a carrier, a surfactant, an anticomplex agent and a combination thereof.

6. An article of manufacture comprising:
   (i) a first bacteriophage capable of infecting the pathogen *Pseudomonas syringae* pv. tomato, the bacteriophage having the genomic nucleic acid sequence as set forth in SEQ ID NO: 19;
   (ii) a second, non-identical bacteriophage capable of infecting the pathogen *Pseudomonas syringae* pv. tomato, the bacteriophage having the genomic nucleic acid sequence as set forth in SEQ ID NO: 17; and
   (iii) a third, non-identical bacteriophage capable of infecting the pathogen *Pseudomonas syringae* pv. tomato, the bacteriophage having the genomic nucleic acid sequence as set forth in SEO ID NO: 21.

7. A method of controlling or preventing bacterial speck disease of a tomato plant comprising contacting the tomato plant with at least three non-identical bacteriophages in an amount which is effective at infecting the plant pathogen *Pseudomonas syringae* pv. tomato, said at least three non-identical bacteriophages having the genomic nucleic acid sequence as set forth in SEQ ID NOs: 19 and 21, thereby controlling or preventing the bacterial speck disease of the tomato plant.

8. The method of claim 7, wherein said contacting is affected at a seedling phase.

9. The method of claim 7, wherein said contacting is in the soil in the vicinity of or onto: a root, a stem, a seed, a fruit, a flower, a leaf, or any combination thereof.

10. The method of claim 7, wherein said contacting comprises dipping, spraying or fogging.

\* \* \* \* \*